US009885656B2

United States Patent
Li et al.

(10) Patent No.: US 9,885,656 B2
(45) Date of Patent: Feb. 6, 2018

(54) LINE SCAN KNIFE EDGE HEIGHT SENSOR FOR SEMICONDUCTOR INSPECTION AND METROLOGY

(71) Applicant: KLA-TENCOR CORPORATION, Milpitas, CA (US)

(72) Inventors: Shifang Li, Pleasanton, CA (US); Paul Horn, Milpitas, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 149 days.

(21) Appl. No.: 14/967,432

(22) Filed: Dec. 14, 2015

(65) Prior Publication Data

US 2016/0178514 A1 Jun. 23, 2016

Related U.S. Application Data

(60) Provisional application No. 62/092,836, filed on Dec. 17, 2014.

(51) Int. Cl.
*G01B 11/28* (2006.01)
*G01N 21/55* (2014.01)
(Continued)

(52) U.S. Cl.
CPC ......... *G01N 21/55* (2013.01); *G01B 11/0608* (2013.01); *G01N 21/8806* (2013.01);
(Continued)

(58) Field of Classification Search
CPC .............. G01N 21/55; G01N 21/8806; G01N 21/9501; G01B 11/0608; G03F 7/70625; G03F 7/70641; G02B 1/11
See application file for complete search history.

(56) References Cited

U.S. PATENT DOCUMENTS 5,155,544 A * 10/1992 Vandenberg ....... G01M 11/0257
356/124
5,159,412 A * 10/1992 Willenborg ........ G01B 11/0616
250/559.07
(Continued)

FOREIGN PATENT DOCUMENTS

EP          1164436 A2    12/2001
JP         58060433 A     4/1983
(Continued)

OTHER PUBLICATIONS

International Search Report, PCT/US20151066505, ISA/US, dated Mar. 30, 2016.
(Continued)

*Primary Examiner* — Michael A Lyons
(74) *Attorney, Agent, or Firm* — Hodgson Russ LLP

(57) ABSTRACT

This semiconductor inspection and metrology system includes a knife-edge mirror configured to receive light reflected from a wafer. The knife-edge mirror is positioned at a focal point of the light reflected from the wafer such that the reflective film on the knife-edge mirror is configured to block at least some of the light reflected from the wafer. The portion of blocked light changes when the light reflected from the wafer is under-focused or over-focused. At least one sensor receives the light reflected from the wafer. Whether the light is under-focused or over-focused can be determined using a reading from the at least one sensor. A height of an illuminated region on the surface of the wafer can be determined using such a reading from the at least one sensor.

20 Claims, 20 Drawing Sheets

(51) Int. Cl.
*G01B 11/06* (2006.01)
*G01N 21/95* (2006.01)
*G01N 21/88* (2006.01)
*G03F 7/20* (2006.01)

(52) U.S. Cl.
CPC ..... *G01N 21/9501* (2013.01); *G03F 7/70625* (2013.01); *G01N 2201/0612* (2013.01)

(56) References Cited

U.S. PATENT DOCUMENTS

| | | |
|---|---|---|
| 5,911,326 A | 6/1999 | Ikeda |
| 5,999,266 A | 12/1999 | Takahashi et al. |
| 6,522,777 B1 | 2/2003 | Paulsen et al. |
| 6,603,103 B1 | 8/2003 | Ulrich et al. |
| 6,603,529 B1 | 8/2003 | Finarov |
| 7,126,699 B1 | 10/2006 | Wihl et al. |
| 7,728,961 B2 | 6/2010 | Watson |
| 7,869,022 B2 | 1/2011 | Van Boxmeer et al. |
| 2006/0033921 A1* | 2/2006 | Den Boef ........... G03F 7/70341 356/446 |
| 2009/0021708 A1 | 1/2009 | Boxmeer et al. |
| 2009/0059216 A1* | 3/2009 | Shibata ............... G01N 21/956 356/237.4 |
| 2011/0317156 A1 | 12/2011 | Lee et al. |
| 2014/0160558 A1* | 6/2014 | Togashi ................ G02B 21/26 359/383 |
| 2017/0067732 A1* | 3/2017 | Li ...................... G01B 11/0608 |

FOREIGN PATENT DOCUMENTS

| | | |
|---|---|---|
| JP | 07004914 A | 1/1995 |
| JP | 2002022415 A | 1/2002 |

OTHER PUBLICATIONS

Vladov et al., "Measuring the apparent beam size of focused ion beam (FIB) systems," 15th European Microscopy Congress, Sep. 2012.

Tortonese et al., "Sub-50 nm isolated line and trench width artifacts for CD metrology," Proc. of SPIE, vol. 5375, 2004, pp. 647-656.

\* cited by examiner

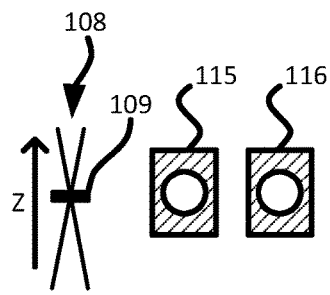
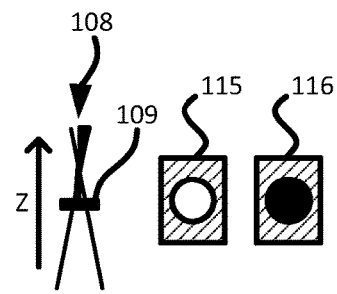
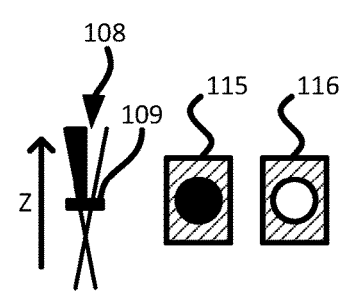
FIG. 2　　　FIG. 3　　　FIG. 4
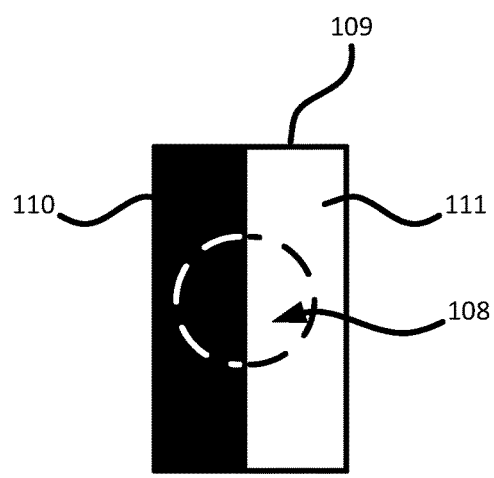
FIG. 5

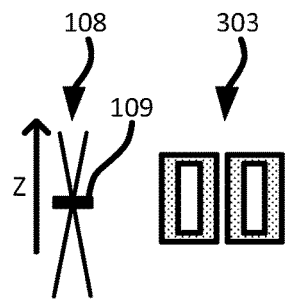 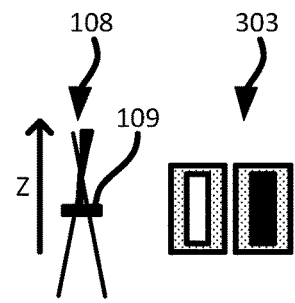 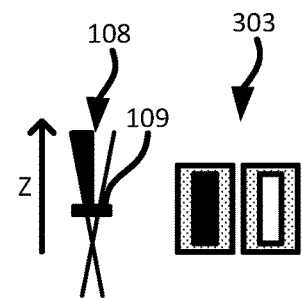
FIG. 11       FIG. 12       FIG. 13
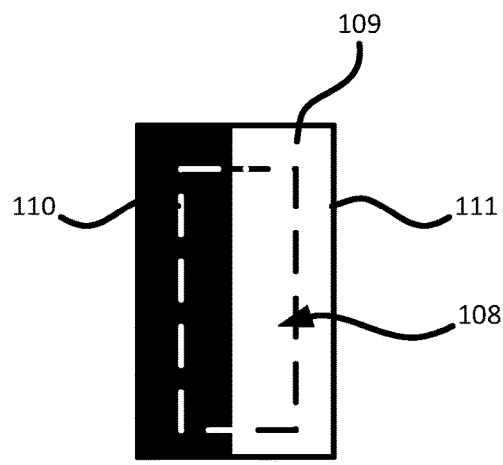
FIG. 14

LINE SCAN KNIFE EDGE HEIGHT SENSOR FOR SEMICONDUCTOR INSPECTION AND METROLOGY

CROSS-REFERENCE TO RELATED APPLICATIONS

This application claims priority to the provisional patent application filed Dec. 17, 2014 and assigned U.S. App. No. 62/092,836, the disclosure of which is hereby incorporated by reference.

FIELD OF THE DISCLOSURE

This disclosure relates to semiconductor wafer inspection and metrology.

BACKGROUND OF THE DISCLOSURE

The semiconductor industry requires three-dimensional ("3D") inspection and/or metrology process for silicon wafers. Such inspection can be used, for example, to test the through silicon via ("TSV") and bump structure or the particle shape (e.g., size and height). Typical techniques for inspection or metrology include: (1) triangulation; (2) geometric shadow; (3) various confocal microscope techniques; and (4) white-light (or broadband light) interferometry. Triangulation and geometric shadow techniques are not precise enough for contemporary back-end of line ("BEOL") applications. Confocal microscopy and interferometry techniques typically fail to meet throughput requirements.

White-light interferometry is known to be a high-resolution method for 3D inspection and metrology and has been used in the semiconductor industry. There are two types of such devices in the market: (1) scanning white-light interferometers ("SWI") and (2) spectroscopic white-light interferometers. In SWI devices, either the sample (e.g., the wafer under inspection) or the inspection optics scan along a direction perpendicular to the wafer surface, such as the z-direction, for a distance. Multiple frames are taken at specific z-values to determine the height measurement for a specific x-y location on the wafer surface. Such SWI devices are robust, but are generally slow. Furthermore, this technique requires the sample to move to a field of view and be stabilized before a measurement is taken, which also limits speed. Likewise, throughputs for current spectroscopic white-light interferometers are also slow for the semiconductor industry.

An auto-focus mechanism is used for an optical probe (OP) in semiconductor inspection and metrology processes. In this technique, a chopper is used to test if the focal point is on, behind, or after the pre-set position. Light passes through the chopper to a bi-cell photodetector. The bi-cell photodetector and chopper are electronically connected with a lock-in amp. When the light is on-focus there is zero phase shift between the reference signal from the chopper and the signals from the two channels of the bi-cell photodetector. If the light is under-focus or over-focus, then the phase of a cell is shifted negative or positive, respectively, to a reference signal, and the phase of another cell is shifted in an opposite direction. With a 100× objective, this method can detect and servo-loop to control the focus better than 20 nm. However, the throughput of the chopper technique is slow.

Existing triangulation and geometric shadow techniques typically do not provide required accuracy and precision for 3D inspection when the target structure height shrinks below 10 μm. Confocal and interferometry methods often do not provide required throughput or are too expensive for 3D inspection. Therefore, what is needed is an inspection and metrology technique that can provide better accuracy, cost, and throughput.

BRIEF SUMMARY OF THE DISCLOSURE

In a first embodiment, a system is provided. The system includes a light source configured to provide light; a stage configured to hold a wafer to receive the light from the light source; a knife-edge mirror; and a sensor configured to receive the light reflected from the wafer. The knife-edge mirror is configured to receive light reflected from the wafer. The knife-edge mirror includes a reflective film and an anti-reflection film that are both disposed on the knife-edge mirror thereby forming a boundary between the reflective film and the anti-reflection film. The knife-edge mirror is positioned at a focal point of the light reflected from the wafer such that the reflective film is configured to block at least some of the light reflected from the wafer. The knife-edge mirror is configured such that a portion of the light blocked by the knife-edge mirror is different when the light reflected from the wafer is under-focused or over-focused. The sensor detects whether the light reflected from the wafer is under-focused or over-focused.

The system can include an objective lens configured to illuminate the wafer with light from the light source and to combine light reflected from the wafer.

The system can include a processor in electrical communication with the sensor. The processor may be configured to determine a height of an illuminated region on a surface of the wafer relative to a normal surface of the wafer.

The sensor can include two photodiodes. The two photodiodes may receive different quantities of the light reflected from the wafer when the light reflected from the wafer is under-focused or over-focused.

The sensor can include a bi-cell photodiode and a prism configured to refract two halves of the light reflected from the wafer onto the bi-cell photodiode.

The system can include a diffractive optics configured to shape the light into a line that is projected onto the wafer. The sensor may include a photo-diode array.

The knife-edge mirror can be positioned at a non-perpendicular angle relative to the light reflected from the wafer. The sensor can include two photodiodes. The system can further include a second sensor configured to receive the light reflected from the wafer that is reflected by the knife-edge mirror. The second sensor can include two photodiodes.

The knife-edge mirror can be positioned at a non-perpendicular angle relative to the light reflected from the wafer. The sensor can include a bi-cell photodiode. The system can further include a second sensor configured to receive the light reflected from the wafer that is reflected by the knife-edge mirror. The second sensor can include a second bi-cell photodiode.

The knife-edge mirror can be positioned at a non-perpendicular angle relative to the light reflected from the wafer. The sensor can include a bi-cell photodiode. The system can further include a diffractive optics configured to shape the light into a line that is projected onto the wafer; a prism configured to refract two halves of the light reflected from the wafer onto the bi-cell photodiode; a second sensor configured to receive the light reflected from the wafer that is reflected by the knife-edge mirror; and a second prism configured to refract two halves of the light reflected from the wafer that is reflected by the knife-edge mirror onto the second bi-cell photodiode. The second sensor can include a second bi-cell photodiode.

The knife-edge mirror can be positioned at a non-perpendicular angle relative to the light reflected from the wafer. The second sensor can include two photo-diode arrays. The system can further include a diffractive optics configured to shape the light into a line that is projected onto the wafer and a second sensor configured to receive the light reflected from the wafer that is reflected by the knife-edge mirror. The second sensor can include two photo-diode arrays.

The stage can be configured to scan the wafer relative to the light from the light source.

In a second embodiment, a method is provided. The method includes reflecting light off a surface of a wafer; passing the light through a knife-edge mirror; receiving light from the knife-edge mirror with at least one sensor; and determining whether the light is under-focused or over-focused using a reading from the at least one sensor. The knife-edge mirror includes a reflective film and an anti-reflection film that are both disposed on the knife-edge mirror thereby forming a boundary between the reflective film and the anti-reflection film. The knife-edge mirror is positioned at a focal point of the light reflected from the wafer such that the reflective film is configured to block at least some of the light reflected from the wafer and such that a portion of the light blocked by the knife-edge mirror is different when the light reflected from the wafer is under-focused or over-focused;

The method may further include determining a height of an illuminated region on a surface of the wafer relative to a normal surface of the wafer. The method may further include determining presence of defects on the wafer.

The wafer can be scanned relative to the light.

The method may further include splitting the light from the knife-edge mirror into two quantities and determining whether the quantities are equal.

The light projected onto the wafer can be shaped into a line.

Part of the light can be reflected from the knife-edge mirror to a second sensor. Whether the light is under-focused or over-focused can be determined using a reading from the second sensor. The method also may further include splitting the light that is reflected from the knife-edge mirror into two quantities and determining whether the quantities are equal.

DESCRIPTION OF THE DRAWINGS

For a fuller understanding of the nature and objects of the disclosure, reference should be made to the following detailed description taken in conjunction with the accompanying drawings, in which:

FIGS. 2-4 represent readings for the photodiodes of FIG. 1 when the light is focused, under-focused, and over-focused, respectively;

FIG. 5 is a schematic of light passing through a knife-edge mirror in accordance with an embodiment of the present disclosure;

FIGS. 11-13 represent readings for the photo-diode array of FIG. 10 when the light is focused, under-focused, and over-focused, respectively;

FIG. 14 is another schematic of light passing through a knife-edge mirror in accordance with an embodiment of the present disclosure;

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

Embodiments of the system and method disclosed herein use the characteristics of phase shift relative to focal point shift to improve throughput. A knife-edge mirror (KEM) is used to determine whether light is focused, under-focused, or over-focused. Though more signals can be used, only two to four signals per x-y point are needed to determine a height of the reflection point on a wafer. This design is more robust and lower cost than existing techniques and can be faster than white light interferometry. Especially for 3D inspection and metrology, embodiments of the system and method disclosed herein provide better throughput, cost, and accuracy compared to existing techniques. For example, throughput can be increased orders of magnitude compared to the chopper technique when using a line scan scheme.

Figure 1:
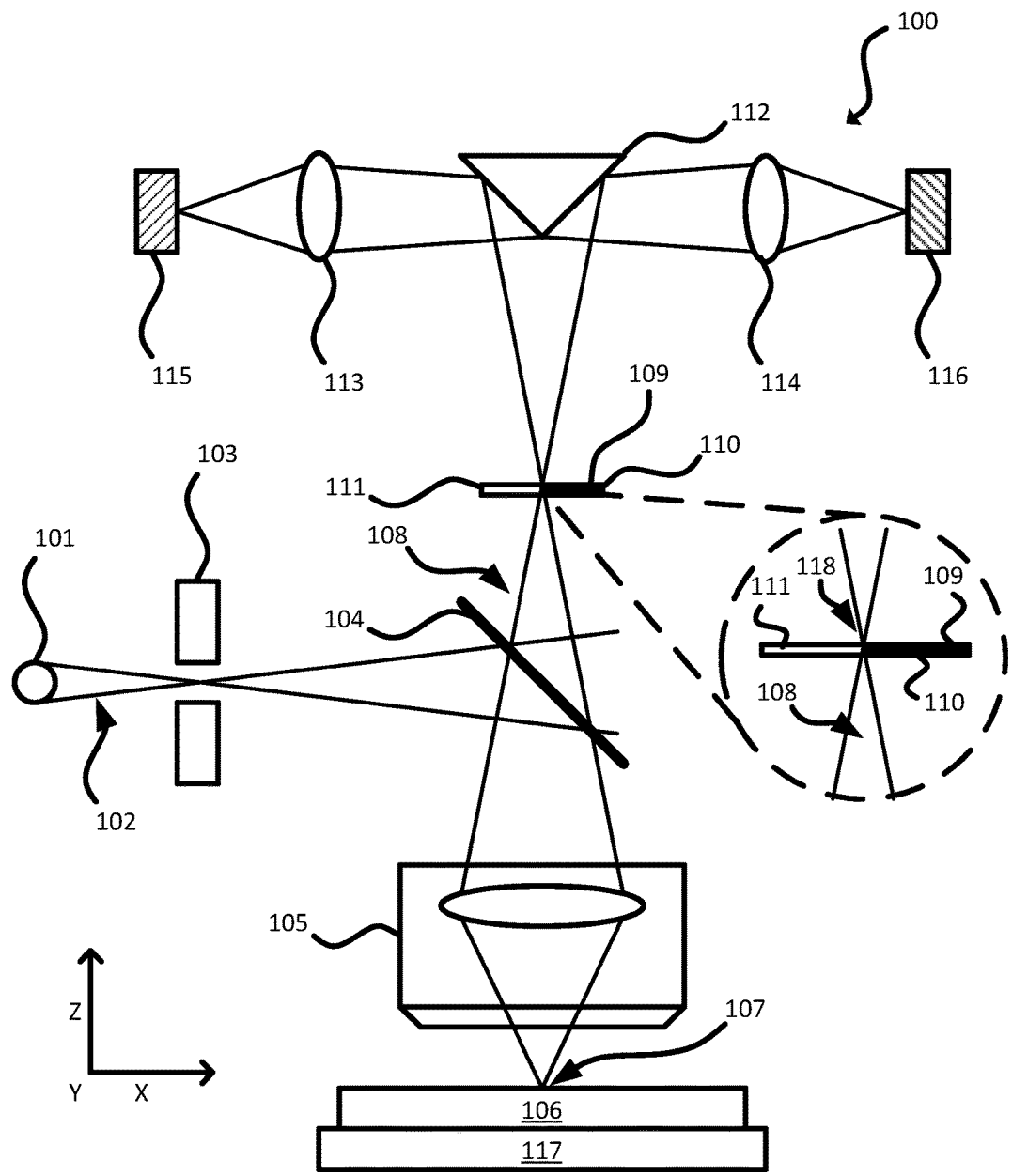
FIG. 1 is an embodiment in accordance with the present disclosure using two photodiodes.

FIG. 1 is an embodiment using two photodiodes 115, 116. The system 100 has a light source 101 that is configured to provide light 102 having a spectrum of wavelength range. In some embodiments, the light source 101 may be configured to provide white light (i.e., broadband light in the visible spectrum) or light that is partially or completely outside of the visible spectrum. In an exemplary embodiment, the light 102 provided by the light source 101 includes wavelengths (λ) from 400-800 nm.

A laser light source can be used for the light source 101, which can provide a higher brightness compared to spectroscopic methods, such as white light interferometry and chromatic confocal microscopy. Laser light sources, such as diode lasers, improve lifetime, stability, and thermal control of the light source. The light source 101 may be, for example, a visible diode laser.

The light 102 is projected toward a source pinhole 103 and a beam splitter 104, which splits the light 102 into two quantities as seen in FIG. 1. The light 102 is then projected through an objective lens 105, which may be a high magnification objective lens. Some or all of the light 102 passes through the objective lens 105 onto at least a portion of a sample at an illumination point 107. The sample may be, for example, a wafer 106. The spot size of the light 102 at the illumination point 107 may be diffraction limited.

The wafer 106 is disposed on a stage 117 configured to position the wafer 106 to receive the light 102. The stage 117 can be fixed or can scan in the x-direction, y-direction, and/or z-direction. The wafer 106 may be clamped to the stage 117 in an instance, such as through mechanical and/or electrostatic clamping. For example, the stage 117 can translate the wafer 106 in a plane perpendicular to the axis of the light 102 or the objective lens 105 (e.g., the x-y plane).

Reflected light 108 from the wafer 106 is projected through the objective lens 105 and a KEM 109. The KEM 109 includes a reflective film 110 and an anti-reflection film 111 disposed on the KEM 109. There is a boundary between the reflective film 110 and the anti-reflection film 111. For example, half the KEM 109 may be coated with the anti-reflection film 111 and half the KEM 109 may be coated with the reflective film 110. The boundary of the reflective film 110 and anti-reflection film 111 is a straight line and can behave like a knife edge in a Foucault test.

The boundary between the reflective film 110 and the anti-reflection film 111 of the KEM 109 is aligned at the focal point of the reflected light 108 at the middle of the focus spot when the surface of the wafer 106 is at its normal z-position. As in the Foucault test, the KEM 109 provides a uniform transmitted light beam when the reflected light 108 passes through the KEM 109. This provides a balanced signal at both photodiodes 115, 116.

The focal point 118 for the reflected light 108 relative to the KEM 109 can be better seen in the inset of FIG. 1. As the boundary of the reflective film 110 and anti-reflection film 111 of the KEM 109 is at the middle of the focal point 118 (the Airy disk), the reflective film 110 shears the reflected light 108 in a manner that the transmitted beam has a uniform intensity distribution across the beam.

Reflected light 108 that passes through the KEM 109 is split into two quantities by a prism 112 with a highly reflective coating on two sides and each constituent beam projects through one of the optional lenses 113, 114 to one of the photodiodes 115, 116. Ideally, the prism 112 is placed at the pupil plane, via a relay lens when needed. The lenses 113, 114 are not necessary in this embodiment and the reflected light 108 can be projected from the prism 112 directly to the one of the photodiodes 115, 116. The photodiodes 115, 116 can provide the same performance in terms of the photo-electron efficiency, time response, and electronic amplification gains.

FIGS. 2-4 represent readings for the photodiodes 115, 116 of FIG. 1 when the light is focused, under-focused, and over-focused, respectively. The light 102 illuminates the wafer 106 at the illumination point 107. If the KEM 109 is at the focal point of the reflected light 108, the emerging beam from KEM 109 is uniform and then the two photodiodes 115, 116 will provide balanced signals, as seen in FIG. 2. However, the illumination point 107 on the wafer 106 may vary or otherwise be at different heights across a surface of the wafer 106. For example, there may be a bump, scratch, unfilled via, or defect on or in the wafer 106. This changes the focal point of the reflected light 108 relative to the KEM 109.

If the height of the surface of the wafer increases from the normal setting in the z-direction, then the focal point of the reflected light 108 is beyond the KEM 109, which makes the reflected light 108 under-focused as seen in FIG. 3. In this instance, the two photodiodes 115, 116 will provide unbalanced signals because the KEM 109 blocks more light emerging to photodiode 116 and less light to photodiode 115. Thus, the emerging beam from the KEM 109 is not uniform.

If the height of the surface of the wafer decreases from the normal setting in the z-direction, then the focal point of the reflected light 108 is before the KEM 109, which makes the reflected light 108 over-focused as seen in FIG. 4. In this instance, the two photodiodes 115, 116 will provide unbalanced signals in an opposite way as the under-focus example in FIG. 3, following the same mechanism.

The system 100 can distinguish whether the detected feature on the wafer 106 is above or below the normal surface of the wafer 106 according to the signals of the two photodiodes 115, 116. Which of the photodiodes 115, 116 receives more or less light can be used to determine if the reflected light 108 is under-focused or over-focused. Thus, if the photodiodes 115, 116 do not receive equal quantities of the reflected light 108, then it can be determined that the detected feature on the wafer 106 is above or below the normal surface of the wafer 106.

FIG. 5 is a schematic of light passing through a KEM 109 based on an illumination point. The reflective film 110 (R=1) is configured to block about half of the reflected light 108 from the wafer by placing the boundary through the middle of the Airy disk, no matter if the reflected light 108 is focused, under-focused, or over-focused. The only difference is that the intensity uniformity changes when the reflected light 108 is focused, under-focused, or over-focused. The anti-reflection film 111 (T=1) is configured to allow part of the reflected light 108 to pass through. In an example, half of an Airy disk formed by the beam spot of the reflected light 108 (shown with dotted lines) in FIG. 5 will be blocked by the reflective film 110.

Figure 6:
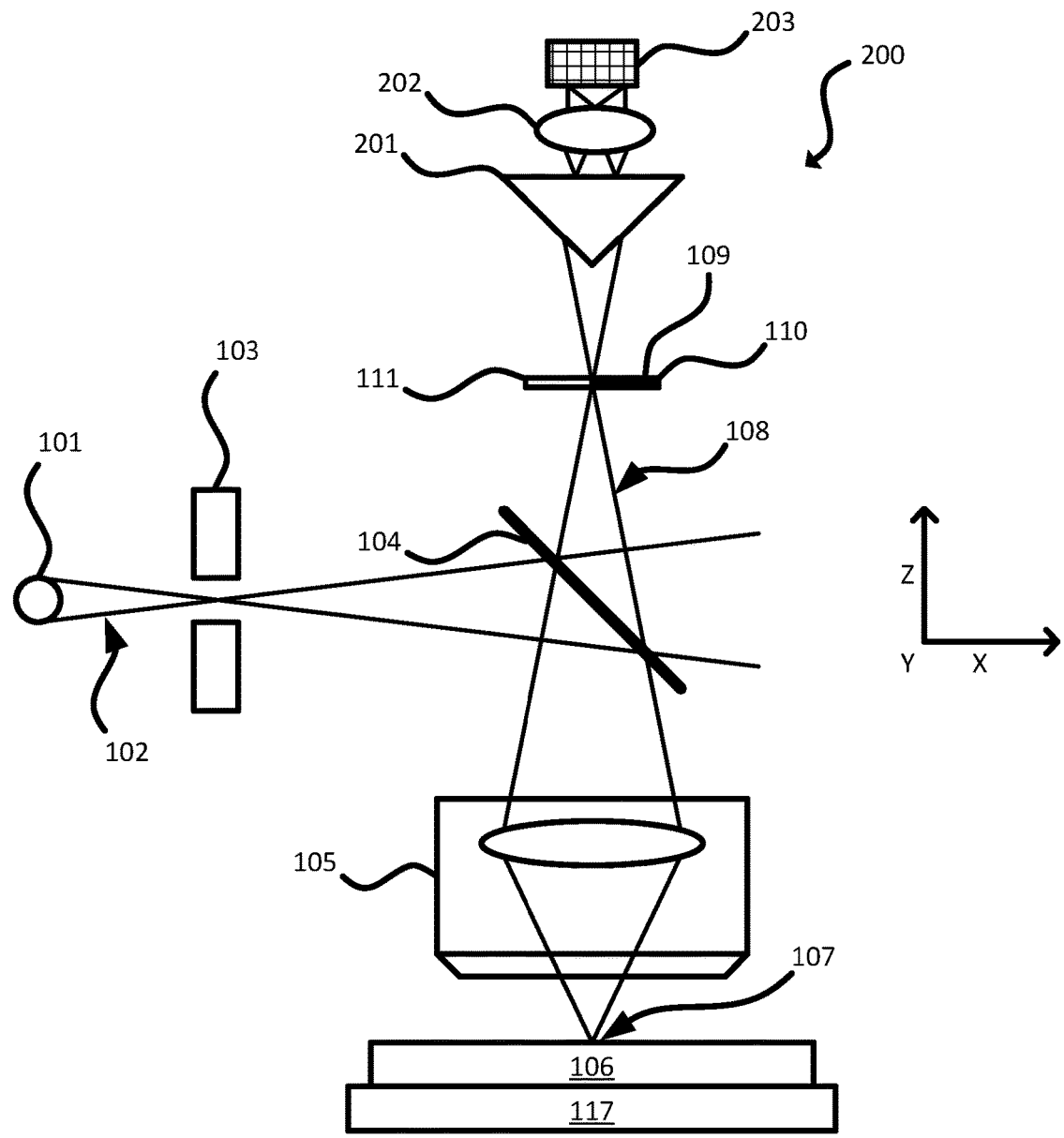
FIG. 6 is an embodiment in accordance with the present disclosure using a bi-cell photodiode.

FIG. 6 is an embodiment using a bi-cell photodiode 203. A bi-cell photodiode, such as the bi-cell photodiode 203, has two active photodiode areas which can measure uniformity of a light beam. In the system 200, a prism 201 refracts two halves of the reflected light 108 onto a bi-cell photodiode 203. This may be through an optional lens 202. The bi-cell photodiode 203 will be balanced when the wafer 106 is in focus.

Figure 7:
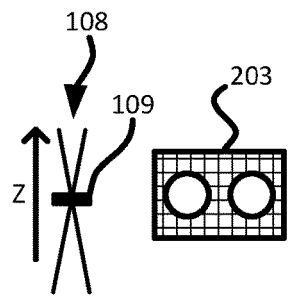
FIGS. 7-9 represent readings for the bi-cell photodiode of FIG. 6 when the light is focused, under-focused, and over-focused, respectively.
Figure 8:
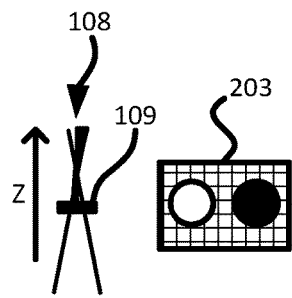
Figure 9:
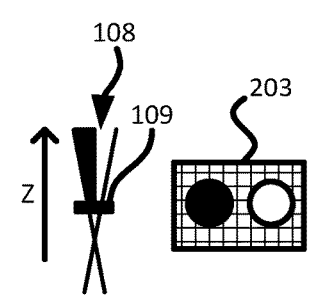

FIGS. 7-9 represent readings for the bi-cell photodiode 203 of FIG. 6 when the light is focused, under-focused, and over-focused, respectively. Height differences on the surface of the wafer 106 changes the focal point of the reflected light

108. If the KEM 109 is at the focal point of the reflected light 108, then the bi-cell photodiode 203 will provide a balanced signal because the emerging beam from the KEM 109 is uniform as seen in FIG. 7. If the height of the surface of the wafer increases from the normal setting in the z-direction, then the focal point of the reflected light 108 is beyond the KEM 109, which makes the reflected light 108 under-focused as seen in FIG. 8. If the height of the surface of the wafer decreases from the normal setting in the z-direction, then the focal point of the reflected light 108 is before the KEM 109, which makes the reflected light 108 over-focused as seen in FIG. 9. The system 200 can distinguish whether the detected feature on the wafer 106 is above or below the normal surface of the wafer 106 according to the signals of the bi-cell photodiode 203.

Figure 10:
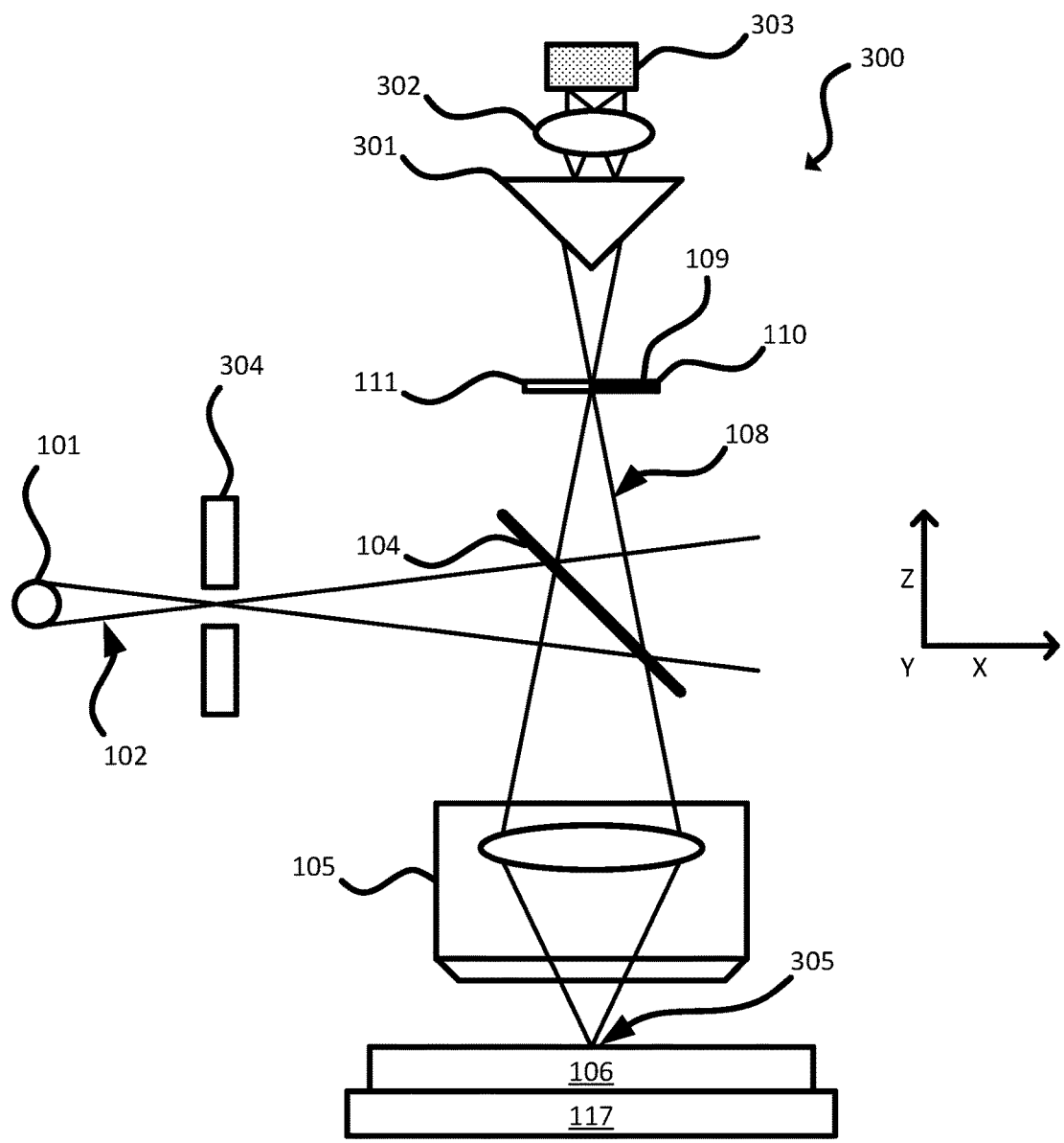
FIG. 10 is an embodiment in accordance with the present disclosure using a photo-diode array.

FIG. 10 is an embodiment using a photo-diode array (PDA) 303. The system 300 uses a source slit 304 to shape the light 102 into a line rather than a point. Such a source slit 304 may have a first dimension (e.g., the "length" of the source slit 304, which may be the y-direction) that is substantially greater than a second dimension (e.g., the "width" of the source slit 304, which may be the z-direction). In some exemplary embodiments, the source slit 304 may be 1 mm to 5 mm in length. For example, in an embodiment, the source slit 304 is 3 mm in length. Other lengths are possible. The width of the source slit 304 is generally sufficiently small that the source slit 304 may be considered to be one-dimensional. For example, the width of the source slit 304 may be similar to a diameter of a point beam in a traditional interferometer. For example, in some embodiments, the source slit 304 may be 5 μm-30 μm in size.

Diffractive optics (not illustrated) also may be included to shape the light 102 into a line rather than a point before the light 102 is incident on the beam splitter 104 or the source slit 304. An illumination line 305 is incident on the wafer 106. The KEM 109 is aligned so that its edge is parallel to the line of the reflected light 108. The boundary of the KEM 109 is aligned to block half of the imaged line of the illumination line 305, no matter if the wafer 106 is focused, under-focused, or over-focused. However, the intensity distribution of the line on the pupil plane will be uniform when the wafer 106 is focused. The spot size of the illumination line 305 may be diffraction limited.

A prism 301 refracts two halves of the reflected light 108 onto a PDA 303 though lens 302. Lens 302 may be required to provide spatial resolution along the illumination line 305 on the wafer 106. A PDA, such as the PDA 303, has an array of multiple areas that can detect a light beam. The PDA 303 will be balanced when the wafer 106 is in focus. If there is a point of wafer 106 on the illumination line 305 with a different height from the normal surface of the wafer 106, then the focal point corresponding to it will be shifted resulting in an unbalanced signal at the corresponding pixels on the PDA 303. The height can be extracted from signals from the PDA 303 based on the unbalanced intensities from the two or more photodiodes in the PDA 303, such as in a pixel-to-pixel manner. The PDA 303 can be, for example, two traditional PDAs aligned side-by-side, or another type of PDA that has 2-by-n pixels (e.g., a PDA with 2 rows). The number of pixels in the PDA 303 can vary.

FIGS. 11-13 represent readings for the PDA 303 of FIG. 10 when the light is focused, under-focused, and over-focused, respectively. Height differences on the surface of the wafer 106 changes the focal point of the reflected light 108. If the focal point of the reflected light 108 is at the KEM 109, then the PDA 303 will provide a balanced signal, as seen in FIG. 11. If the height of the surface of the wafer increases from the normal setting in the z-direction, then the focal point of the reflected light 108 is beyond the KEM 109, which makes the reflected light 108 under-focused as seen in FIG. 12. If the height of the surface of the wafer decreases from the normal setting in the z-direction, then the focal point of the reflected light 108 is before the KEM 109, which makes the reflected light 108 over-focused as seen in FIG. 13. The system 300 can distinguish whether the detected feature on the wafer 106 is above or below the normal surface of the wafer 106 according to the signals of the PDA 303.

FIG. 14 is another schematic of light passing through a KEM 109 based on an illumination line, which can use the same mechanism as FIG. 5. The reflective film 110 (R=1) is configured to block half of the reflected light 108 (shown with dotted lines) from the wafer no matter if the reflected light 108 is focused, under-focused, or over-focused. The anti-reflection film 111 (T=1) is configured to allow the rest of the reflected light 108 to pass through. The focus spot has a finite size (an Airy disk) instead of an infinite small geometric point when the beam is focused. The boundary of the KEM 109 always reflects half of the beam and transmit half of the beam. When the focus changed, the only difference is the uniformity changes when the beams emerge from the KEM 109.

Figure 15:
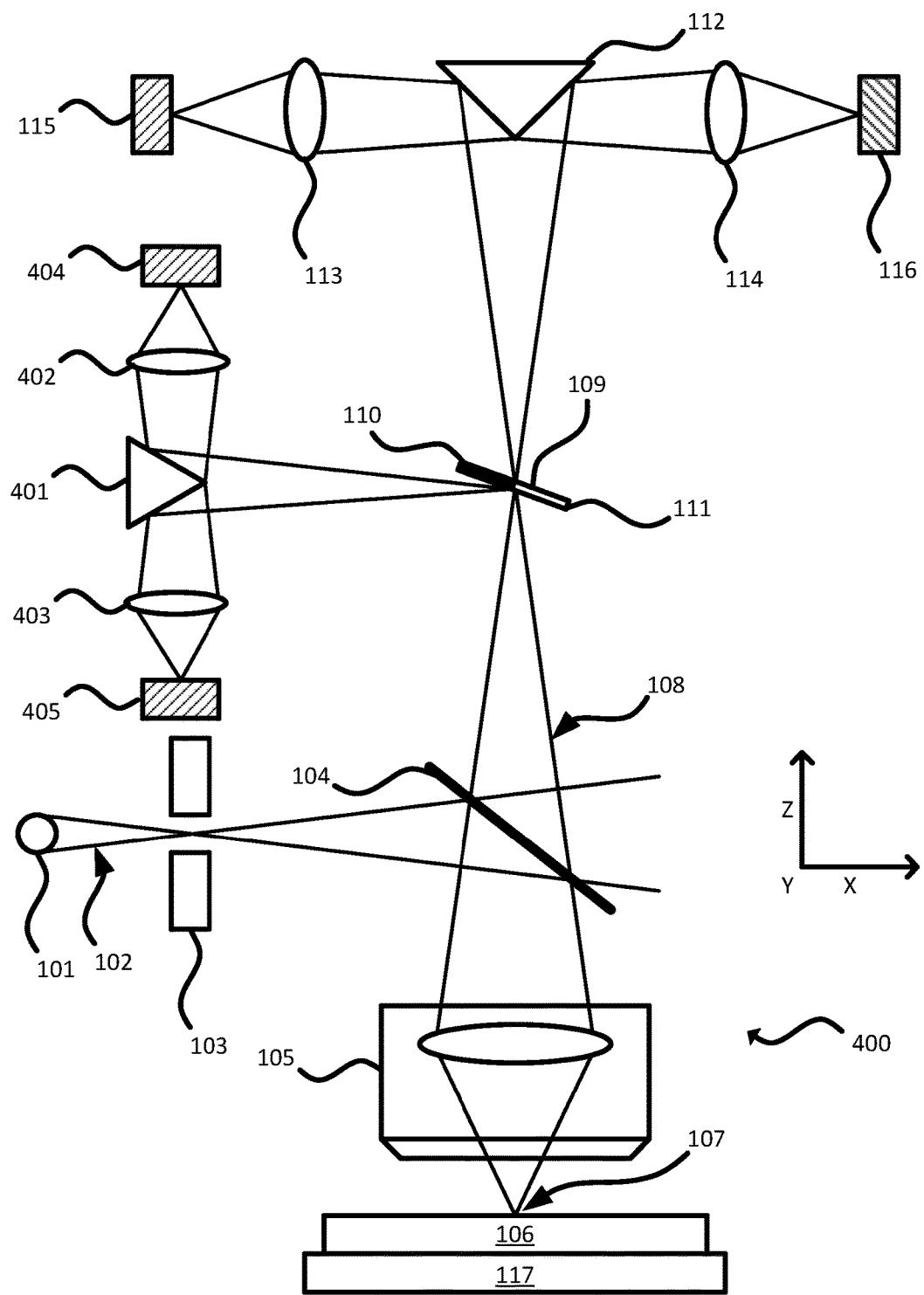
FIG. 15 is an embodiment in accordance with the present disclosure using four photodiodes.
Figure 16:
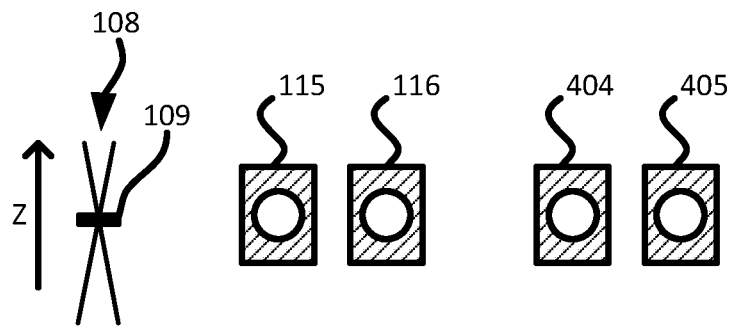
FIGS. 16-18 represent readings for the photodiodes of FIG. 15 when the light is focused, under-focused, and over-focused, respectively.
Figure 17:
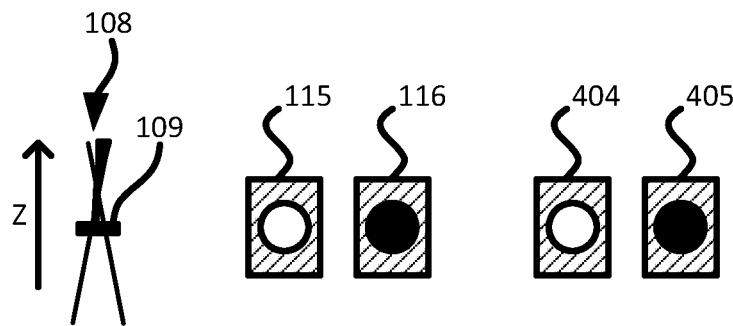
Figure 18:
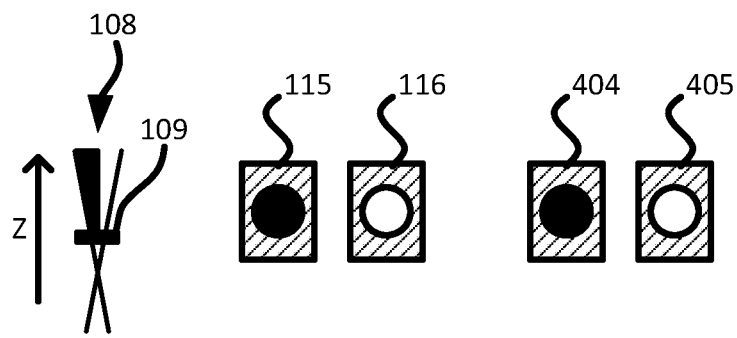

FIG. 15 is an embodiment using four photodiodes 115, 116, 404, 405. In the system 400, the KEM 109 is tilted at an angle so that the beam section emerging from the R=1 range (i.e., from the reflective film 110) is delivered to the photodiodes 404, 405 through a prism 401 and one of the optional lenses 402, 403. The KEM 109 can be tilted to be at a non-perpendicular angle relative to the reflected light 108 (e.g., an axis of the reflected light 108). The lenses 402, 403 are not necessary and the reflected light 108 can be projected directly from the prism 401 to the one of the photodiodes 404, 405. The signals of the photodiodes 404, 405 provide redundant and complimentary measurement that can be used to improve accuracy and precision. For example, the photodiodes 115, 116, 404, 405 can provide multiple measurements, so that the final results can be the average of them. Thus, if there is systematic error, the systematical error can be split into symmetric and asymmetric parts, and the asymmetric part can be averaged out in the final calculation FIGS. 16-18 represent readings for the photodiodes 115, 116, 404, 405 of FIG. 15 when the light is focused, under-focused, and over-focused, respectively. Height differences on the surface of the wafer 106 changes the focal point of the reflected light 108. If the focal point of the reflected light 108 is at the KEM 109, then the photodiodes 115, 116, 404, 405 will provide a balanced signal, as seen in FIG. 16. If the height of the surface of the wafer increases from the normal setting in the z-direction, then the focal point of the reflected light 108 is beyond the KEM 109, which makes the reflected light 108 under-focused as seen in FIG. 17. If the height of the surface of the wafer decreases from the normal setting in the z-direction, then the focal point of the reflected light 108 is before the KEM 109, which makes the reflected light 108 over-focused as seen in FIG. 18. The system 400 can distinguish whether the detected feature on the wafer 106 is above or below the normal surface of the wafer 106 according to the signals of the photodiodes 115, 116, 404, 405.

Figure 19:
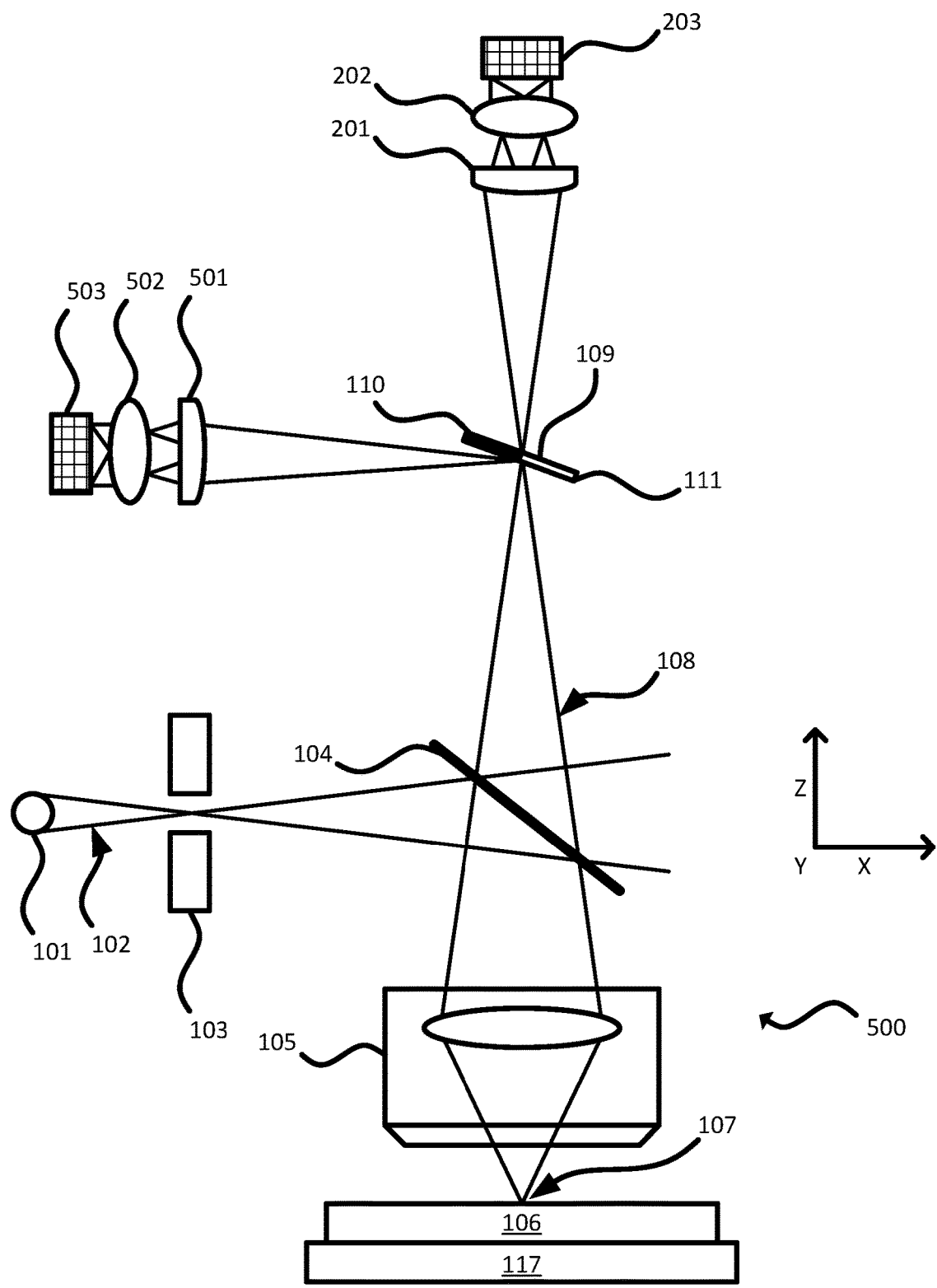
FIG. 19 is an embodiment in accordance with the present disclosure using two bi-cell photodiodes.
Figure 37:
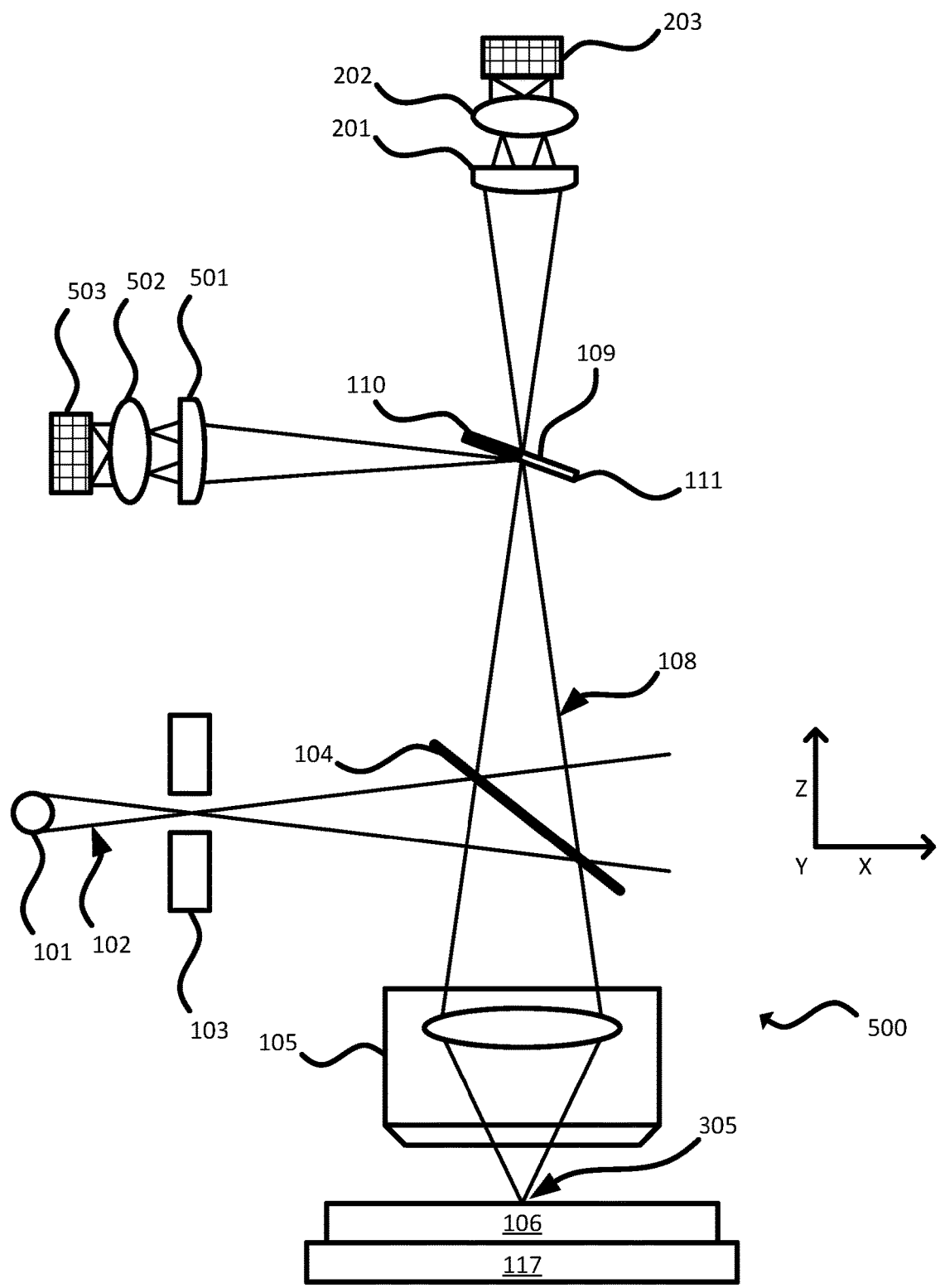
FIG. 37 is a second embodiment in accordance with the present disclosure using two bi-cell photodiodes.

FIGS. 19 and 37 are embodiments using two bi-cell photodiodes 203, 503. In the system 500, the KEM 109 is tilted so that the beam section emerging from the R=1 range (i.e., from the reflective film 110) is delivered to a prism 501, which refracts two halves of the beam section onto a bi-cell photodiode 503. This may be through an optional lens 502. The bi-cell photodiode 503 will be balanced when the wafer 106 is in focus. The signals of the bi-cell photodiodes 203, 503 provide redundant and complimentary measurement that can be used to improve accuracy and precision.

Figure 20:
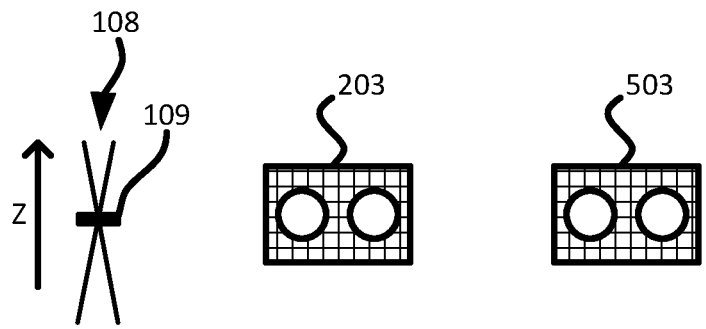
FIGS. 20-22 represent readings for the bi-cell photodiodes of FIG. 19 when the light is focused, under-focused, and over-focused, respectively.
Figure 21:
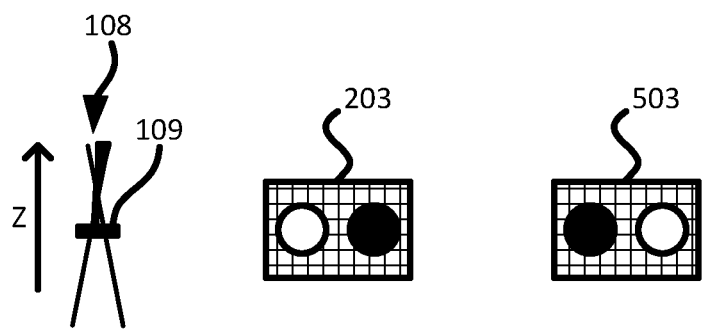
Figure 22:
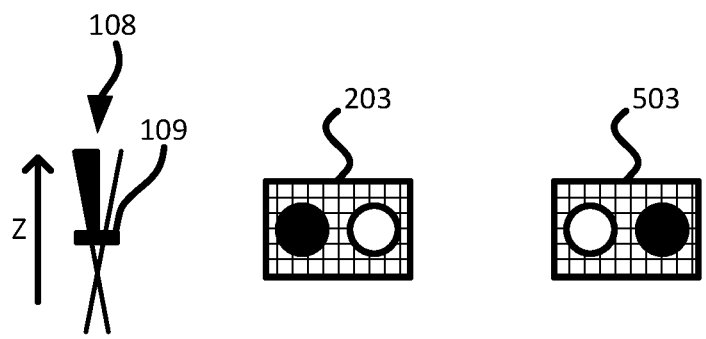
Figure 38:
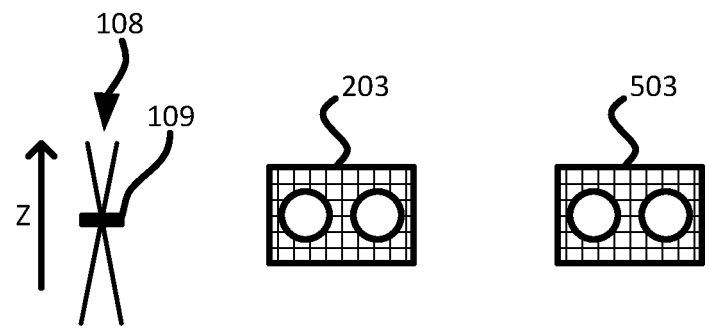
FIGS. 38-40 represent readings for the bi-cell photodiodes of FIG. 37 when the light is focused, under-focused, and over-focused, respectively.
Figure 39:
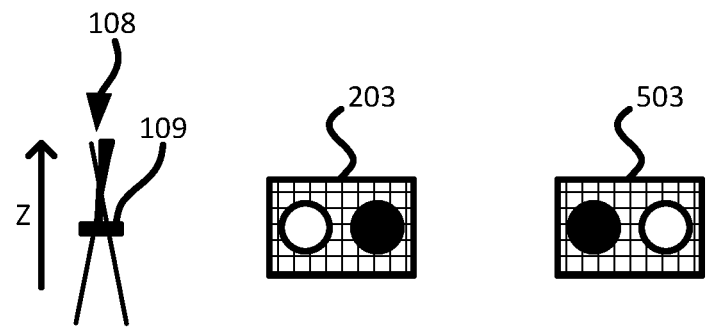
Figure 40:
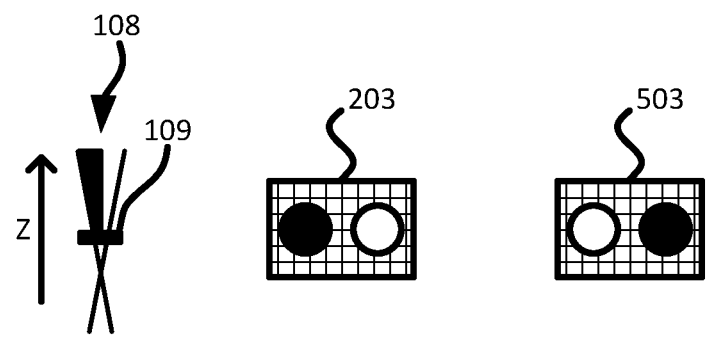

FIGS. 20-22 represent readings for the bi-cell photodiodes 203, 503 of FIG. 19 when the light is focused, under-focused, and over-focused, respectively. FIGS. 38-40 represent readings for the bi-cell photodiodes 203, 503 of FIG. 37 when the light is focused, under-focused, and over-focused, respectively. Height differences on the surface of the wafer 106 changes the focal point of the reflected light 108. If the focal point of the reflected light 108 is at the KEM 109, then the bi-cell photodiodes 203, 503 will provide a balanced signal, as seen in FIG. 20 or FIG. 38. If the height of the surface of the wafer increases from the normal setting in the z-direction, then the focal point of the reflected light 108 is beyond the KEM 109, which makes the reflected light 108 under-focused as seen in FIG. 21 or FIG. 39. If the height of the surface of the wafer decreases from the normal setting in the z-direction, then the focal point of the reflected light 108 is before the KEM 109, which makes the reflected light 108 over-focused as seen in FIG. 22 or FIG. 40. The system 500 can distinguish whether the detected feature on the wafer 106 is above or below the normal surface of the wafer 106 according to the signals of the bi-cell photodiodes 203, 503.

Figure 23:
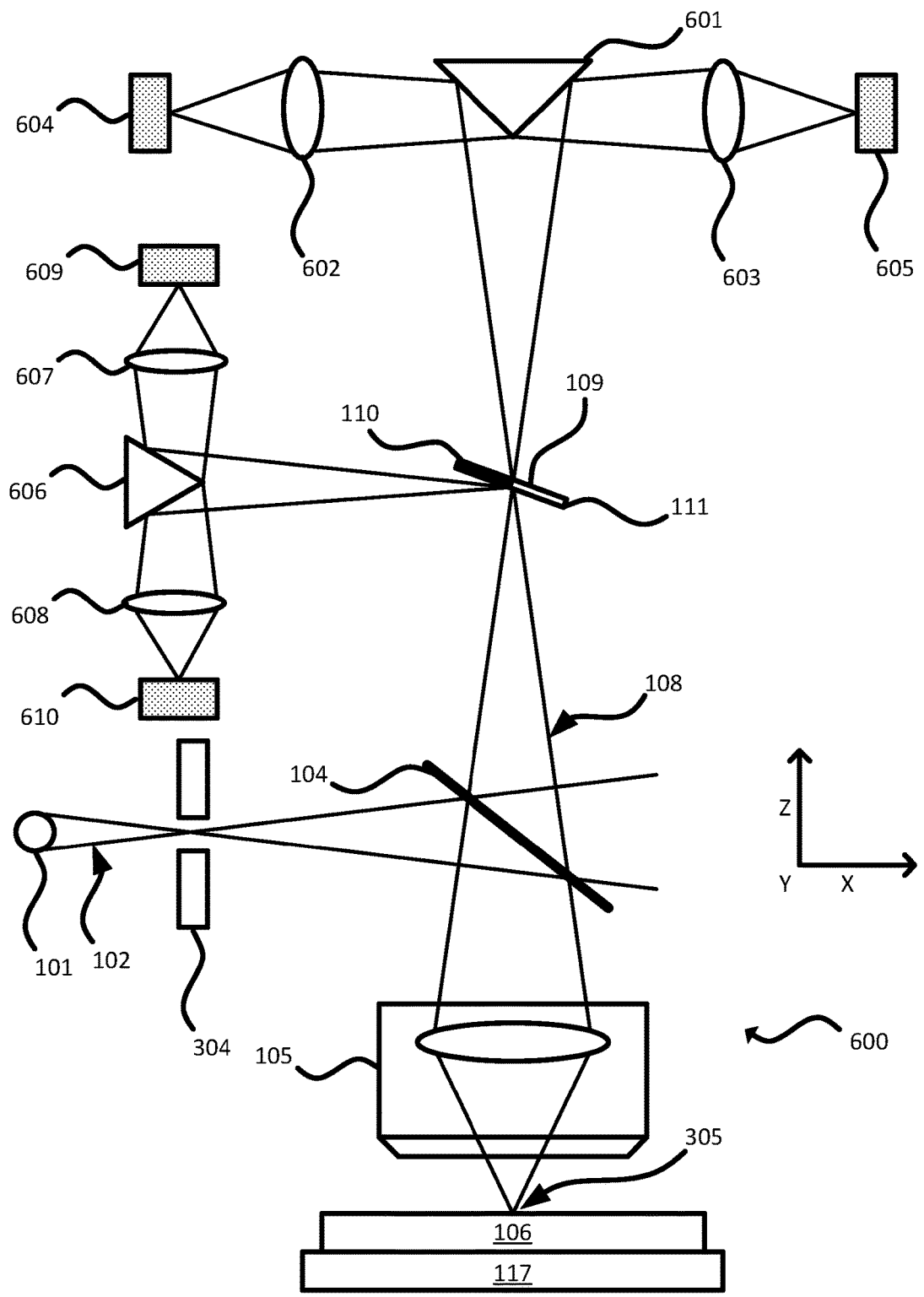
FIG. 23 is an embodiment in accordance with the present disclosure using four photo-diode arrays.

FIG. 23 is an embodiment using four PDAs 604, 605, 609, 610. The system 600 uses a source slit 304 to shape the light 102 into a line rather than a point. Diffractive optics (not illustrated) also may be included to shape the light 102 into a line rather than a point before the light 102 is incident on the beam splitter 104 or the source slit 304. An illumination line 305 is incident on the wafer 106. The KEM 109 is aligned so that its edge is parallel to the line of the reflected light 108.

A prism 601 refracts two halves of the reflected light 108 onto two PDAs 604, 605. Lenses 602, 603 are positioned between the prism 601 and the PDAs 604, 605 to provide spatial resolution along the illumination line 305. The PDAs 604, 605 will be balanced when the wafer 106 is in focus. If there is a point of wafer 106 on the illumination line 305 with a different height from the normal surface of the wafer 106, then the focal point corresponding to it will be shifted resulting in a different balance signal at the corresponding pixels on the PDAs 604, 605. The signal from the PDAs 604, 605 can be extracted based on the unbalanced intensity signal from the two photodiodes in each of the PDAs 604, 605, such as in a pixel-to-pixel manner.

In the system 600, the KEM 109 is tilted so that the beam section emerging from the R=1 range (i.e., from the reflective film 110) is delivered to a prism 606, which refracts two halves of the beam section onto the PDAs 609, 610. The lenses 607, 608 provide spatial resolution along the illumination line 305. The PDAs 609, 610 will be balanced when the wafer 106 is in focus. The signals of the PDAs 609, 610 provide redundant and complementary measurement that can be used to improve accuracy and precision.

Figure 24:
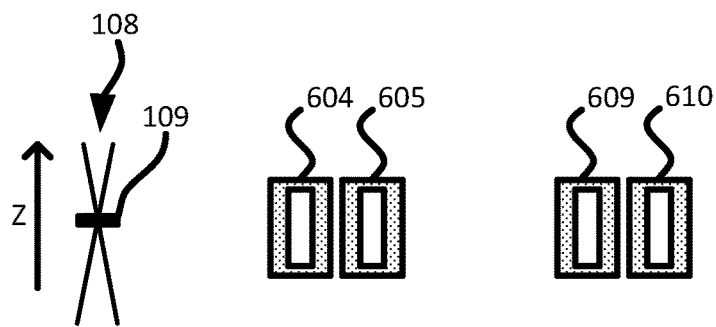
FIGS. 24-26 represent readings for the photo-diode arrays of FIG. 23 when the light is focused, under-focused, and over-focused, respectively.
Figure 25:
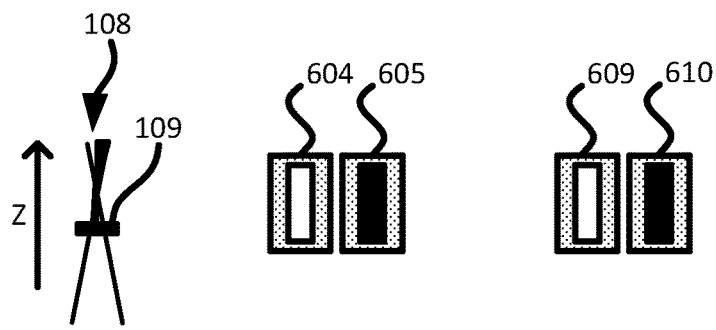
Figure 26:
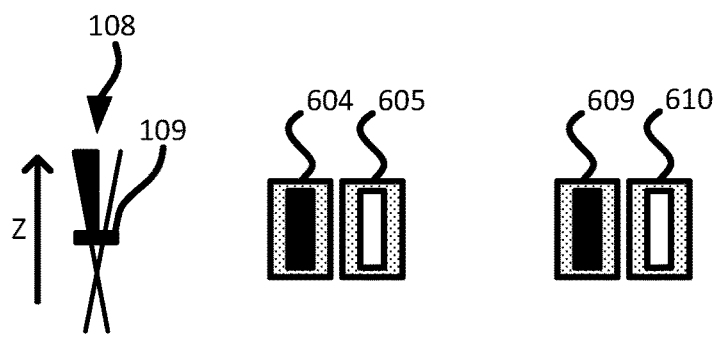

FIGS. 24-26 represent readings for the PDAs 604, 605, 609, 610 of FIG. 23 when the light is focused, under-focused, and over-focused, respectively. Height differences on the surface of the wafer 106 changes the focal point of the reflected light 108. If the focal point of the reflected light 108 is at the KEM 109, then the PDAs 604, 605, 609, 610 will provide a balanced signal, as seen in FIG. 24. If the height of the surface of the wafer increases from the normal setting in the z-direction, then the focal point of the reflected light 108 is beyond the KEM 109, which makes the reflected light 108 under-focused as seen in FIG. 25. If the height of the surface of the wafer decreases from the normal setting in the z-direction, then the focal point of the reflected light 108 is before the KEM 109, which makes the reflected light 108 over-focused as seen in FIG. 26. The system 600 can distinguish whether the detected feature on the wafer 106 is above or below the normal surface of the wafer 106 according to the signals of the PDAs 604, 605, 609, 610.

Figure 27:
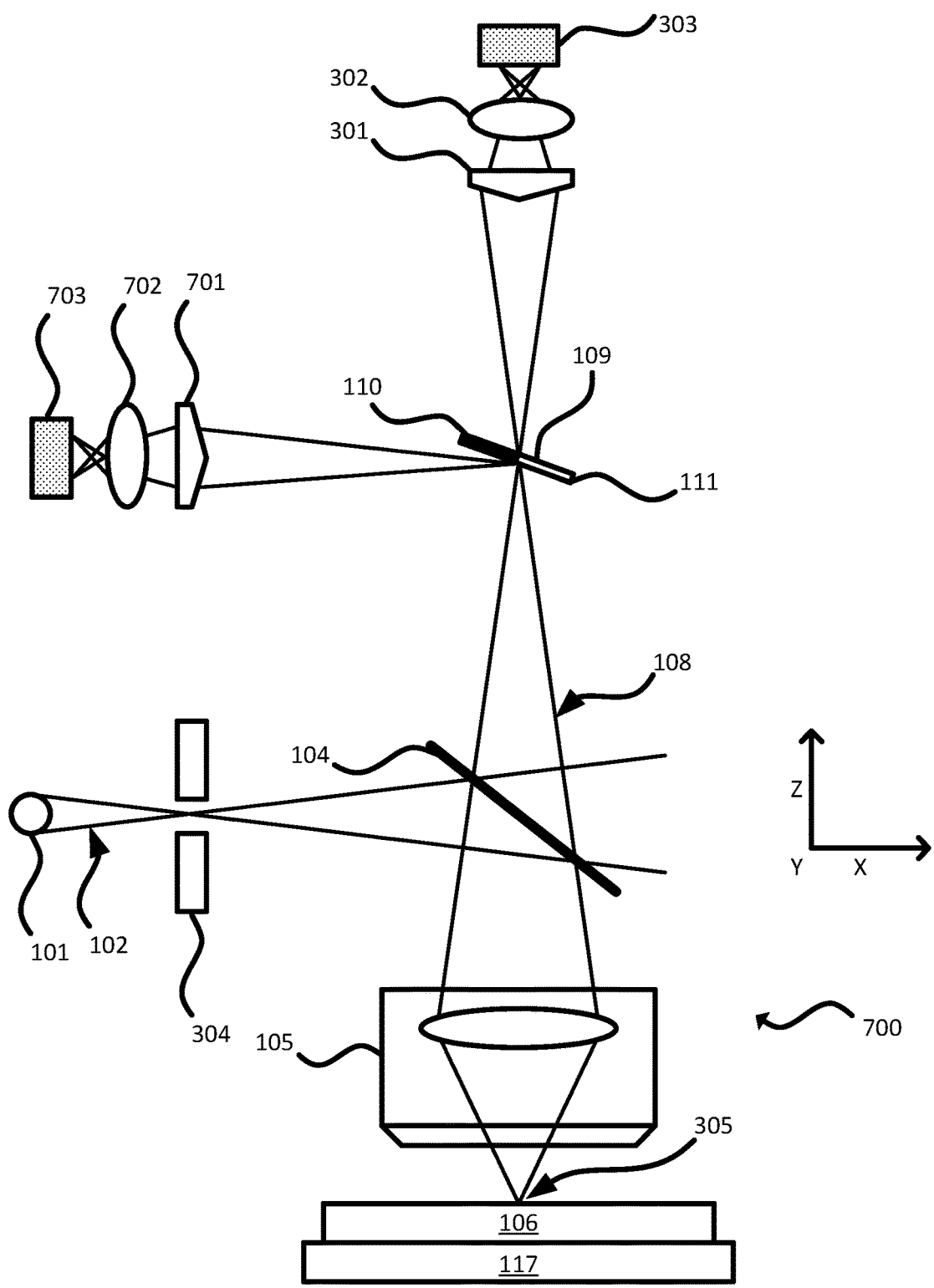
FIG. 27 is an embodiment in accordance with the present disclosure using two photo-diode arrays.

FIG. 27 is an embodiment using two PDAs 303, 703. In the system 700, the KEM 109 is tilted so that the beam section emerging from the R=1 range (i.e., from the reflective film 110) is delivered to a prism 701, which refracts two halves of the beam section onto the PDA 703 through a lens 702 to provide spatial resolution along the illumination line 305. The PDA 703 will be balanced when the wafer 106 is in focus. The signals of the PDA 703 provides redundant measurement that can be used to improve accuracy and precision.

Figure 28:
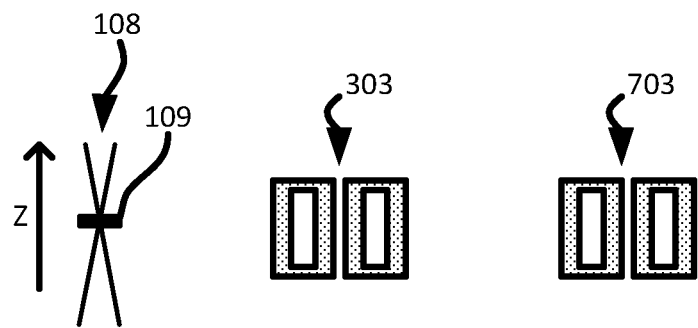
FIGS. 28-30 represent readings for the photo-diode arrays of FIG. 27 when the light is focused, under-focused, and over-focused, respectively.
Figure 29:
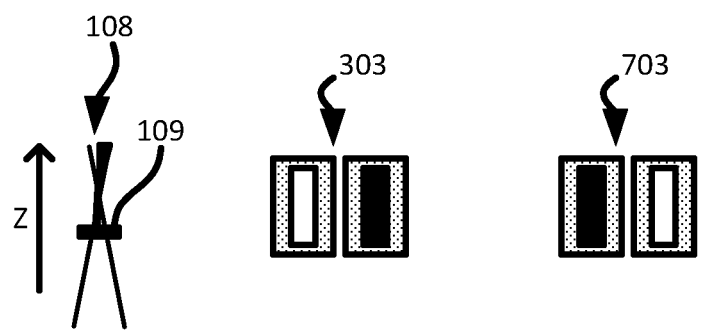
Figure 30:
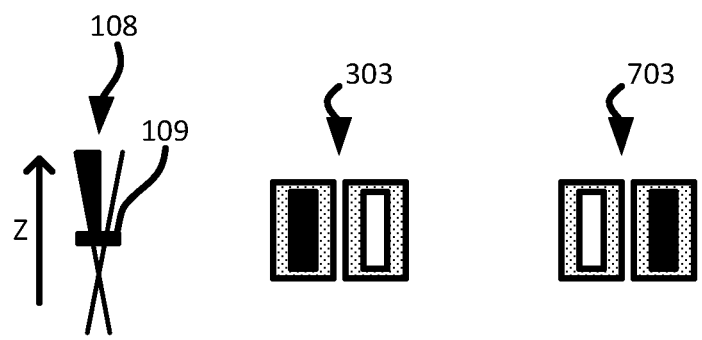

FIGS. 28-30 represent readings for the PDAs 303, 703 of FIG. 27 when the light is focused, under-focused, and over-focused, respectively. Height differences on the surface of the wafer 106 changes the focal point of the reflected light 108. If the focal point of the reflected light 108 is at the KEM 109, then the PDAs 303, 703 will provide a balanced signal, as seen in FIG. 28. If the height of the surface of the wafer increases from the normal setting in the z-direction, then the focal point of the reflected light 108 is beyond the KEM 109, which makes the reflected light 108 under-focused as seen in FIG. 29. If the height of the surface of the wafer decreases from the normal setting in the z-direction, then the focal point of the reflected light 108 is before the KEM 109, which makes the reflected light 108 over-focused as seen in FIG. 30. The system 700 can distinguish whether the detected feature on the wafer 106 is above or below the normal surface of the wafer 106 according to the signals of the PDAs 303, 703.

Figure 31:
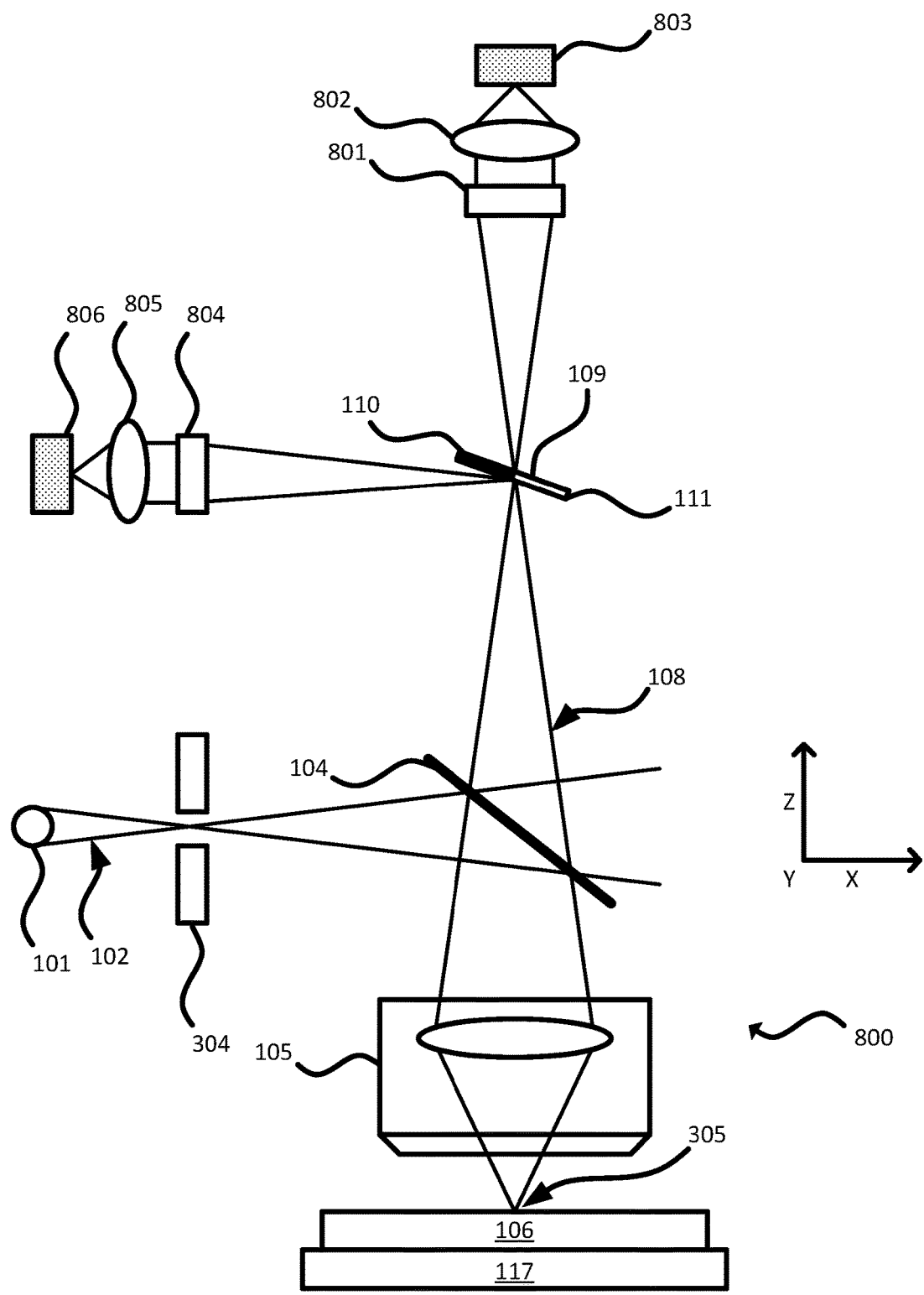
FIG. 31 is another embodiment in accordance with the present disclosure using two photo-diode arrays.

FIG. 31 is another embodiment using two PDAs 803, 806. Reflected light 108 is delivered to a prism 801, which refracts two halves of the beam section onto the PDA 803 through a lens 802 to provide spatial resolution along the illumination line 305. The PDA 803 will be balanced when the wafer 106 is in focus.

In the system 800, the KEM 109 is tilted so that the beam section emerging from the R=1 range (i.e., from the reflective film 110) is delivered to a prism 804, which refracts two halves of the beam section onto the PDA 806. This may be through an optional lens 805. The PDA 806 will be balanced when the wafer 106 is in focus. The signals of the PDA 806 provides redundant and complementary measurement that can be used to improve accuracy and precision.

Figure 32:
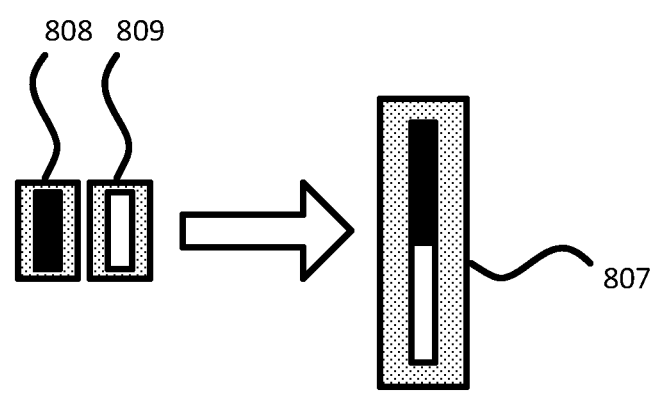
FIG. 32 is a schematic representing reshaping the image in a photo-diode array.

The PDAs 803, 806 may be configured like the PDA 807 in FIG. 32. Images of the line emerging from the KEM can be further reshaped by a beam-stitch technique so that the left and right halves of the line image are stitched as shown in FIG. 32. A difference between the left and right halves of the image line can be detected simultaneously with the same PDA 807. Thus, the action of two PDAs 808, 809 can be performed by a single PDA 807. This may provide a more accurate result.

Figure 33:
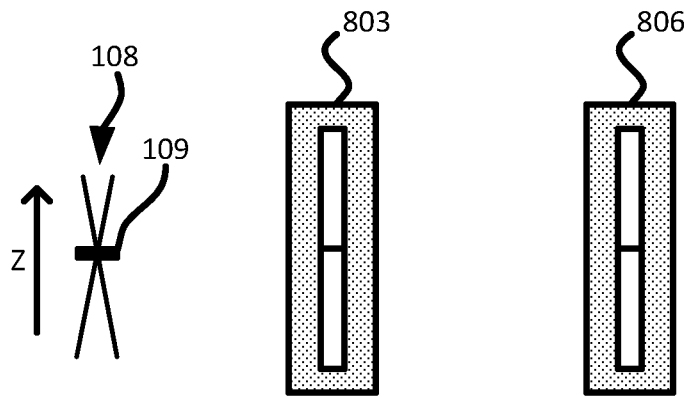
FIGS. 33-35 represent readings for the photo-diode arrays of FIG. 31 when the light is focused, under-focused, and over-focused, respectively.
Figure 34:
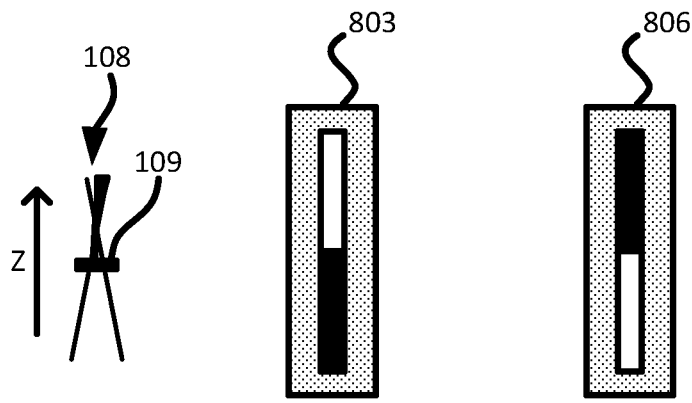
Figure 35:
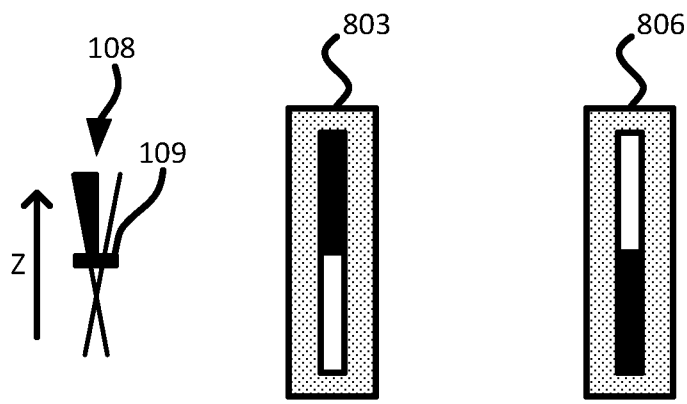

FIGS. 33-35 represent readings for the PDAs 803, 806 of FIG. 31 when the light is focused, under-focused, and over-focused, respectively. Height differences on the surface of the wafer 106 changes the focal point of the reflected light 108. If the focal point of the reflected light 108 is at the KEM 109, then the PDAs 803, 806 will provide a balanced signal, as seen in FIG. 33. If the height of the surface of the wafer increases from the normal setting in the z-direction, then the focal point of the reflected light 108 is beyond the KEM 109, which makes the reflected light 108 under-focused as seen in FIG. 34. If the height of the surface of the wafer decreases from the normal setting in the z-direction, then the focal point of the reflected light 108 is before the KEM 109, which makes the reflected light 108 over-focused as seen in FIG. 35. The system 800 can distinguish whether the detected feature on the wafer 106 is above or below the normal surface of the wafer 106 according to the signals of the PDAs 803, 806.

Figure 36:
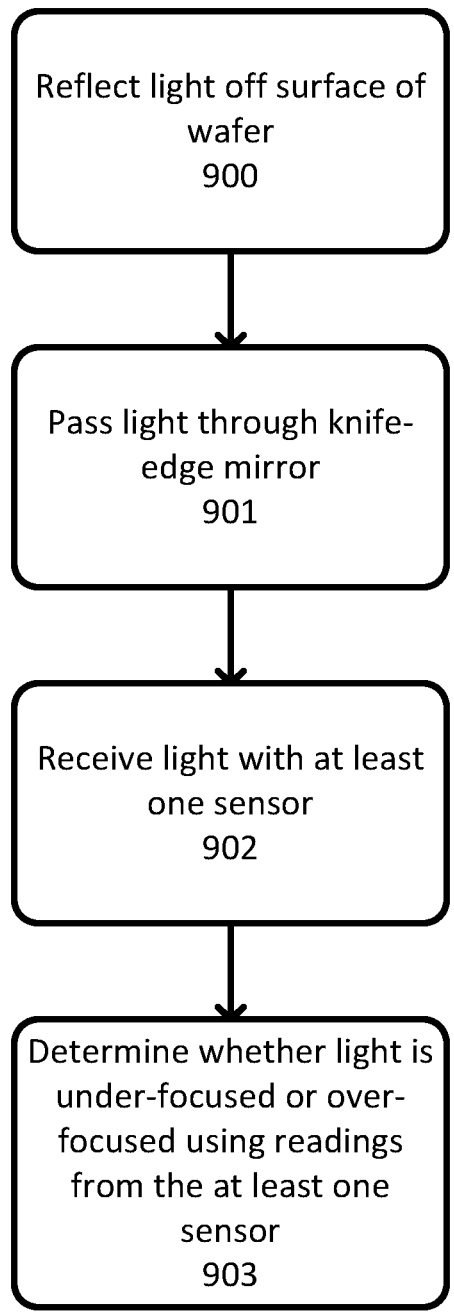
FIG. 36 is a flowchart of a method in accordance with the present disclosure.

FIG. 36 is a flowchart of a method. In 900, light is reflected off a surface of a wafer, such as the wafer 106. In 901, the reflected light passes through a KEM. In 902, the reflected light from the KEM is received by at least one sensor. In 903, it is determined whether the light is under-focused or over-focused using readings from the at least one sensor. The resulting determination regarding under-focusing or over-focusing can be used to determine the height of the surface of the wafer or if defects are present on the surface of the wafer.

Some or all of the sensors disclosed herein (e.g., photo-diodes, bi-cell photodiodes, PDAs) can be electronically connected to a controller. The controller can include a processor, an electronic storage device in electronic communication with the processor, and a communication port in electronic communication with the processor. The processor can receive readings from the sensors, such as through an electronic connection. Using the readings from the sensors, the processor can be configured to determine a height of an illuminated region of the wafer surface (e.g., point or line) or whether a defect is present on or in the wafer surface.

The wafer may scan relative to the light in the x-direction and/or y-direction using the stage in the embodiments disclosed herein. This can provide surface topography information for an area of the surface of the wafer. This area may be, for example, a patch image, a full wafer inspection, or desired points as a bump-height inspection.

It should be noted that embodiments disclosed herein may determine a surface height profile of a wafer without scanning in the z-direction, although the stage may be capable of movement in the z-direction for other purposes.

Embodiments of the systems disclosed herein may need to be calibrated. Calibration can include determining the relationship of the relative signal difference (e.g., the ratio of the difference of pixels to the sum of them) to a known height difference.

Power to the laser light source can be controlled, such as through modulating or pulsing, which can enable strobing. In an instance, during operation of embodiments disclosed herein, the optics can be kept steady or otherwise fixed and the wafer can move in a direction perpendicular to the illumination line in synchronization with a PDA readout timer. Strobe technology, such as that caused by modulating the laser and synchronizing the laser with the PDA readout, can provide further spatial improvement because strobing can reduce blurring due to motion of a stage, such as the stage 117.

Embodiments of the systems disclosed herein can be used for inspection or metrology of a wafer. A height of the wafer surface or whether defects are present on or in the wafer surface can be used as feedback during semiconductor manufacturing.

Multiple design parameters of embodiments of the systems disclosed herein can be optimized. For example, height sensitivity, which relates to the depth of focus, is inversely proportional to the square of the objective numerical aperture (NA). The relative high NA may be adjusted, though many applications require an NA of greater than 0.25. A high NA objective typically provides a smaller field of view, which results in higher spatial (x- and y-) resolution and slower operation.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. A system comprising:
a light source configured to provide light;
a stage configured to hold a wafer to receive the light from the light source;
a knife-edge mirror configured to receive light reflected from the wafer, wherein the knife-edge mirror includes a reflective film and an anti-reflection film that are both disposed on the knife-edge mirror thereby forming a boundary between the reflective film and the anti-reflection film, wherein the knife-edge mirror is positioned at a focal point of the light reflected from the wafer such that the reflective film is configured to block at least some of the light reflected from the wafer, and wherein the knife-edge mirror is configured such that a portion of the light blocked by the knife-edge mirror is different when the light reflected from the wafer is under-focused or over-focused; and
a sensor configured to receive the light reflected from the wafer, wherein the sensor detects whether the light reflected from the wafer is under-focused or over-focused.

2. The system of claim 1, further comprising an objective lens configured to illuminate the wafer with light from the light source and to combine light reflected from the wafer.

3. The system of claim 1, further comprising a processor in electrical communication with the sensor, wherein the processor is configured to determine a height of an illuminated region on a surface of the wafer relative to a normal surface of the wafer.

4. The system of claim 1, wherein the sensor comprises two photodiodes, wherein the two photodiodes receive different quantities of the light reflected from the wafer when the light reflected from the wafer is under-focused or over-focused.

5. The system of claim 1, wherein the sensor comprises a bi-cell photodiode and the system further comprises a prism configured to refract two halves of the light reflected from the wafer onto the bi-cell photodiode.

6. The system of claim 1, further comprising a diffractive optics configured to shape the light into a line that is projected onto the wafer and wherein the sensor comprises a photo-diode array.

7. The system of claim 1, wherein the knife-edge mirror is positioned at a non-perpendicular angle relative to the light reflected from the wafer, wherein the sensor comprises two photodiodes, and further comprising a second sensor configured to receive the light reflected from the wafer that is reflected by the knife-edge mirror, wherein the second sensor comprises two photodiodes.

8. The system of claim 1, wherein the knife-edge mirror is positioned at a non-perpendicular angle relative to the light reflected from the wafer, wherein the sensor comprises a bi-cell photodiode and the system further comprises a second sensor configured to receive the light reflected from the wafer that is reflected by the knife-edge mirror, wherein the second sensor comprises a second bi-cell photodiode.

9. The system of claim 1, wherein the knife-edge mirror is positioned at a non-perpendicular angle relative to the light reflected from the wafer, wherein the sensor comprises a bi-cell photodiode and the system further comprises:
- a diffractive optics configured to shape the light into a line that is projected onto the wafer;
- a prism configured to refract two halves of the light reflected from the wafer onto the bi-cell photodiode;
- a second sensor configured to receive the light reflected from the wafer that is reflected by the knife-edge mirror, wherein the second sensor comprises a second bi-cell photodiode; and
- a second prism configured to refract two halves of the light reflected from the wafer that is reflected by the knife-edge mirror onto the second bi-cell photodiode.

10. The system of claim 1, wherein the knife-edge mirror is positioned at a non-perpendicular angle relative to the light reflected from the wafer, wherein the sensor comprises two photo-diode arrays, and the system further comprises:
- a diffractive optics configured to shape the light into a line that is projected onto the wafer; and
- a second sensor configured to receive the light reflected from the wafer that is reflected by the knife-edge mirror, wherein the second sensor comprises two photo-diode arrays.

11. The system of claim 1, wherein the stage is configured to scan the wafer relative to the light from the light source.

12. A method comprising:
reflecting light off a surface of a wafer;
passing the light through a knife-edge mirror, wherein the knife-edge mirror includes a reflective film and an anti-reflection film that are both disposed on the knife-edge mirror thereby forming a boundary between the reflective film and the anti-reflection film, and wherein the knife-edge mirror is positioned at a focal point of the light reflected from the wafer such that the reflective film is configured to block at least some of the light reflected from the wafer and such that a portion of the light blocked by the knife-edge mirror is different when the light reflected from the wafer is under-focused or over-focused;
receiving light from the knife-edge mirror with at least one sensor; and
determining whether the light is under-focused or over-focused using a reading from the at least one sensor.

13. The method of claim 12, further comprising determining a height of an illuminated region on a surface of the wafer relative to a normal surface of the wafer.

14. The method of claim 12, further comprising determining presence of defects on the wafer.

15. The method of claim 12, further comprising scanning the wafer relative to the light.

16. The method of claim 12, further comprising:
splitting the light from the knife-edge mirror into two quantities; and
determining whether the quantities are equal.

17. The method of claim 12, further comprising shaping the light projected onto the wafer into a line.

18. The method of claim 12, further comprising reflecting part of the light from the knife-edge mirror to a second sensor.

19. The method of claim 18, further comprising determining whether the light is under-focused or over-focused using a reading from the second sensor.

20. The method of claim 19, further comprising:
splitting the light that is reflected from the knife-edge mirror into two quantities; and
determining whether the quantities are equal.

* * * * *